United States Patent
Teles

(10) Patent No.: US 6,846,961 B2
(45) Date of Patent: Jan. 25, 2005

(54) PREPARATION OF 1-METHOXY-2-PROPANOL

(75) Inventor: Joaquim Henrique Teles, Otterstadt (DE)

(73) Assignee: BASF Aktiengesellschaft, Ludwigshafen (DE)

(*) Notice: Subject to any disclaimer, the term of this patent is extended or adjusted under 35 U.S.C. 154(b) by 0 days.

(21) Appl. No.: 10/309,253

(22) Filed: Dec. 4, 2002

(65) Prior Publication Data

US 2003/0166975 A1 Sep. 4, 2003

(30) Foreign Application Priority Data

Dec. 28, 2001 (DE) .......................................... 101 64 348

(51) Int. Cl.$^7$ .............................................. C07C 41/03
(52) U.S. Cl. ...................................... 568/698; 568/678
(58) Field of Search ................................. 568/698, 678

(56) References Cited

U.S. PATENT DOCUMENTS

| | | | |
|---|---|---|---|
| 5,266,283 A | | 11/1993 | Friesen et al. |
| 5,342,903 A | * | 8/1994 | Wolleb et al. ............... 525/407 |
| 5,637,739 A | | 6/1997 | Jacobsen et al. |
| 5,665,890 A | * | 9/1997 | Jacobsen et al. ............ 549/230 |
| 5,929,232 A | | 7/1999 | Jacobsen et al. |
| 5,945,568 A | * | 8/1999 | Nagata et al. ............... 568/618 |
| 6,262,278 B1 | | 7/2001 | Jacobsen et al. |
| 6,348,607 B1 | | 2/2002 | Müller et al. ................ 549/523 |
| 2002/0149544 A1 | | 10/2002 | Rosen et al. ................... 345/6 |

FOREIGN PATENT DOCUMENTS

| | | |
|---|---|---|
| CA | 2339710 | 2/2001 |
| DE | 198 35 907 | 2/2000 |
| DE | 198 47 629 | 4/2000 |
| DE | 199 36 547 | 2/2001 |
| DE | 100 01 401 | 7/2001 |
| DE | 100 15 246 | 10/2001 |
| DE | 100 32 884 | 1/2002 |
| DE | 100 32 885 | 1/2002 |
| DE | 101 05 527 | 8/2002 |
| EP | 0 100 119 | 2/1984 |
| JP | 2000 063314 | 2/2000 |
| WO | WO 96/28402 | 9/1996 |
| WO | WO 00/09463 | 2/2000 |
| WO | WO 01/47865 | 7/2000 |
| WO | WO 01/51475 | 7/2001 |
| WO | WO 01/72729 | 10/2001 |
| WO | WO 01/89690 | 11/2001 |
| WO | WO 02/02544 | 1/2002 |
| WO | WO 02/02545 | 1/2002 |
| WO | WO 02/062779 | 8/2002 |
| WO | WO 02/085516 | 10/2002 |

OTHER PUBLICATIONS

Jacobsen et al., "Enantioselective Catalytic Ring Opening of Expoxides with Carboxylic Acids", Tetrahedron Letters, vol. 38, No. 5, pp. 773–776, 1997.

Paddock, Robert L. et al., "Chemical C02 Fixation: Cr (III) Salen Complexes as Highly Efficient Catalysts for the Coupling of C02 and Epoxides", Journal of the American Chemical Society, 2001, 123(46), pp. 11498–11499.

J. M. Ready, et al., J. Am. Chem. Soc., vol. 123, no. 11, pp. 2687–2688, "Highly Active Oligomeric (Salen) Co Catalysts for Asymmetric Epoxide Ring–Opening Reactions", 2001.

* cited by examiner

Primary Examiner—Rosalynd Keys
(74) Attorney, Agent, or Firm—Oblon, Spivak, McClelland, Maier & Neustadt, P.C.

(57) ABSTRACT

Process for preparing 1-methoxy-2-propanol by reacting propylene oxide with methanol in the presence of a racemic catalyst which comprises an asymmetric polydentate (tetradentate) ligand complexed with a metal atom, where the complex has an approximately planar geometry.

24 Claims, No Drawings

PREPARATION OF 1-METHOXY-2-PROPANOL

The present invention relates to a process for the selective preparation of 1-methoxy-2-propanol by reaction of propylene oxide (PO) with methanol in the presence of a novel catalyst system, and also to this catalyst system per se.

One of the important resultant secondary products of propylene oxide is 1-methoxy-2-propanol. It is used both as solvent and as starting material for numerous preparative processes.

1-Methoxy-2-propanol has hitherto been prepared industrially by addition of methanol, which is used in a large excess, onto propylene oxide using NaOH as catalyst. This gives a mixture of the desired 1-methoxy-2-propanol (90%) and 5% each of 2-methoxy-1-propanol and dipropylene glycol monomethyl ether as isomer mixture. A problem with this reaction, which nevertheless proceeds with a comparatively high selectivity, is the fact that it would be preferable to obtain only, i.e. 100%, 1-methoxy-2-propanol. This is because, inter alia, 2-methoxy-1-propanol is classified as teratogenic. Thus, in-spec 1-methoxy-2-propanol which is saleable and suitable for further processing can only be prepared with the aid of a costly distillation for removing the undesirable by-products. The by-products obtained then have to be disposed of, which represents a further expense.

In J. Am. Chem. Soc. (2001), 123, 2687–2688, Jacobsen et al. describe the use of oligomeric, enantiomerically pure Co-salen catalysts for the asymmetric ring opening of epoxides. Inter alia, the enantioselective synthesis of enantiomerically pure 2-methoxy-1-hexanol by reaction of hexene 1-epoxide with methanol is described there. Further such enantiomerically pure salen catalysts are described in detail in WO 00/09463, with this patent application being directed exclusively at enantioselective syntheses using such catalysts.

In view of this prior art, it is an object of the present invention to provide an improved process for preparing racemic 1-methoxy-2-propanol starting from propylene oxide.

We have found that this and further objects are achieved by a process for preparing racemic 1-methoxy-2-propanol by reacting propylene oxide with methanol in the presence of a racemic catalyst which comprises an asymmetric polydentate (tetradentate) ligand complexed with a metal atom, where the complex has an approximately planar coordination geometry.

There are no restrictions in respect of the catalysts which can be used according to the present invention, as long as they meet the abovementioned conditions, i.e. a tetradentate ligand having the properties specified in more detail above. Thus, in particular, the compounds disclosed in WO 00/09463 can be used for the purposes of the present invention, but, in contrast to WO 00/09463, racemic compounds are used as catalysts in the process of the present invention. Thus, the preparation of these compounds is carried out in a manner essentially analogous to the abovementioned international patent application, but the chiral reagents used there are replaced by racemates.

In the process of the present invention, preference is given to using one or more of the following catalysts having the formulae (A) to (D).

Catalysts having the following formula (A):

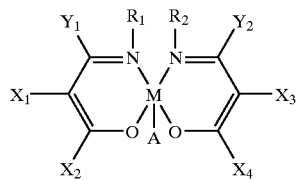

where
the substituents $R_1$, $R_2$, $Y_1$, $Y_2$, $X_1$, $X_2$, $X_3$ and $X_4$, are each, independently of one another, one of the following groups of atoms:
hydrogen, halogen, alkyl, alkenyl, alkynyl, hydroxyl, amino, nitro, diol, amine, imine, amide, phosphoryl, phosphonate, phosphine, carbonyl, carboxyl, silyl, ether, thioether, sulfonyl, selenoether, ketone, aldehyde, ester and $-(CH_2)_m-R_7$, where one or more of the abovementioned substituents may together form a carbocyclic or heterocyclic ring having from 4 to 8 atoms in the ring, with the proviso that to form β-iminocarbonyls as tetradentate ligands to which they are bound, at least one of $R_1$, $Y_1$, $X_1$ and $X_2$ is covalently bound to at least one of $R_2$, $Y_2$, $X_3$ and $X_4$, and at least one of Y1 and $Y_2$ is hydrogen;
$R_7$ is an aryl, cycloalkyl or cycloalkenyl group, a heterocyclic group or a polycyclic group;
m is an integer in the range from 0 to 8;
M is the metal atom;
A is a counterion or a nucleophile; and
the catalyst is present as a racemic mixture.
Catalysts having the following formula (B):

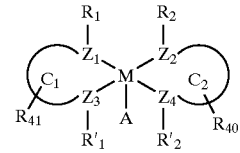

where
$Z_1$, $Z_2$, $Z_3$ and $Z_4$ are each, independently of one another, a Lewis base; the $C_1$ moiety, viewed as a combination of $Z_1$, $Z_3$ and M, and the $C_2$ moiety, viewed as a combination of $Z_2$, $Z_4$ and M, in each case form, independently of one another, a heterocycle;
$R_1$, $R_2$, $R'_1$ and $R'_2$, in each case independently of one another, are either absent or represent a covalently bound organic or inorganic substituent, in each case depending on the valence of the electron-donating atom to which they are bound;
$R_{40}$ and $R_{41}$, in each case independently of one another, are either absent or represent one or more covalently bound organic or inorganic substituents on $C_1$ and $C_2$, depending on the valence of the ring atom to which they are bound, or two or more of $R_1$, $R_2$, $R'_1$, $R'_2$, $R_{40}$ and $R_{41}$ together form a bridging substituent;
with the proviso that $C_1$ is substituted in at least one position by $R_1$, $R'_1$ or $R_{41}$ and $C_2$ is substituted in at least one position by $R_2$, $R'_2$ or $R_{40}$, and at least one of $R_1$, $R'_1$ and $R_{41}$ together with at least one of $R_2$, $R'_2$ and $R_{40}$ form a bridging substituent, where $Z_1$, $Z_2$, $Z_3$ and $Z_4$ are present as a tetradentate ligand;
M is a metal atom,
A is a counterion or a nucleophile; and
the catalyst is present as a racemic mixture.

Catalysts having the following formula (C):

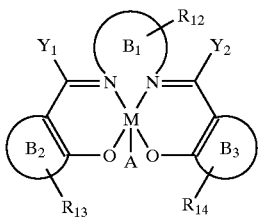

where
the $B_1$ moiety is a bridging substituent of the diimine type, represented by $-R_{15}-R_{16}-R_{17}$, where $R_{15}$ and $R_{17}$, in each case independently of one another, are absent or represent an alkyl, alkenyl or alkynyl group and $R_{16}$ is either absent or is an amine, imine, amide, phosphoryl, carbonyl, silyl, oxygen, sulfur, sulfonyl, selenium or ester group or atom;

$B_2$ and $B_3$ are each, independently of one another, rings selected from among cycloalkyl, cycloalkenyl, aryl and heterocyclic rings, where the rings have from 4 to 8 atoms in the ring;

$Y_1$ and $Y_2$ are each, independently of one another, hydrogen, halogen, alkyl, alkenyl, alkynyl, hydroxyl, amino, nitro, diol, amine, imine, amide, phosphoryl, phosphonate, phosphine, carbonyl, carboxyl, silyl, ether, thioether, sulfonyl, selenoether, ketone, aldehyde, ester or $-(CH_2)_m-R_7$ groups or atoms;

$R_{12}$, $R_{13}$ and $R_{14}$, in each case independently of one another, are absent or represent one or more covalently bound halogen, alkyl, alkenyl, alkynyl, hydroxyl, amino, nitro, diol, amine, imine, amide, phosphoryl, phosphonate, phosphine, carbonyl, carboxyl, silyl, ether, thioether, sulfonyl, selenoether, ketone, aldehyde, ester and $-(CH_2)_m-R_7$ substituents on $B_1$, $B_2$ and $B_3$, where $R_{12}$ may occur at one or more positions on $R_{15}-R_{16}-R_{17}$, or two or more of the groups $R_{12}$, $R_{13}$, $R_{14}$, $Y_1$ and $Y_2$ together form a bridging substituent;

$R_7$ is an aryl, cycloalkyl or cycloalkenyl group, a heterocyclic group or a polycyclic group;

m is an integer in the range from 0 to 8;

M is the metal atom;

A is a counterion or a nucleophile; and the catalyst is present as a racemic mixture.

Catalysts having the following formula (D):

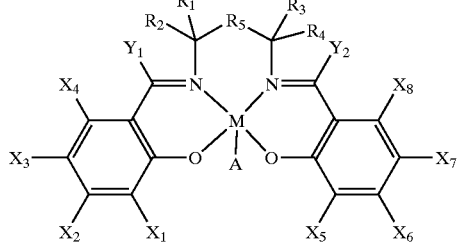

where
the substituents $R_1$, $R_2$, $R_3$, $R_4$, $R_5$, $Y_1$, $Y_2$, $X_1$, $X_2$, $X_3$, $X_4$, $X_5$, $X_6$, $X_7$ and $X_8$ are each, independently of one another, hydrogen, halogen, alkyl, alkenyl, alkynyl, hydroxyl, amino, nitro, diol, amine, imine, amide, phosphoryl, phosphonate, phosphine, carbonyl, carboxyl, silyl, ether, thioether, sulfonyl, selenoether, ketone, aldehyde, ester or $-(CH_2)_m-R_7$ groups or atoms;

or two or more of the substituents together form a carbocycle or heterocycle having from 4 to 10 atoms in the ring;

$R_7$ is an aryl, cycloalkyl or cycloalkenyl group, a heterocyclic group or a polycyclic group;

m is an integer in the range from 0 to 8;

M is the metal atom;

A is a counterion or a nucleophile;

where, if $R_5$ is absent, at least one of $R_1$ and $R_2$ together with at least one of $R_3$ and $R_4$ form a bridging substituent; and the catalyst is present as a racemic mixture.

Furthermore, it is also possible to use oligomers of the above-described compounds of the formulae (A) to (D) in place of the monomeric compounds themselves, with the number of repeating units preferably being from 2 to 20, in particular from 2 to 6.

The preparation and preferred embodiments of the abovementioned catalysts are described in WO 00/09463 and in the abovementioned article by Jacobsen in J. Am. Chem. Soc., 2001, 123, 2687–2688. Thus, reference may be made to these two documents for further details regarding the catalysts which can be used in the present process.

As regards the metal atoms used within the catalysts, all transition metals (i.e. metals having d electrons) can be used. Preference is given to using transition metals of groups 5 to 12 which are coordinatively unsaturated and are not present in their highest oxidation state. Particularly useful metals include Cr, Mn, V, Fe, Co, Mo, W, Ru and Ni. Particular preference is given to metals of group VI, very particularly preferably Cr(III) and Co(III).

Co(II) can also be used when the reaction conditions are selected so that it is oxidized in situ to Co(III) (e.g. in the presence of $O_2$ or other suitable oxidizing agents, including electrochemical oxidation).

As regards the nucleophiles A which can be used for the purposes of the present invention, reference may once again be made to WO 00/09463, in particular pages 55/56. For the purposes of the present invention, preference is given to using nucleophiles containing oxygen atoms, more preferably carboxylates and in particular acetate.

The amount of the catalyst lies generally in a region less than 25 mol %. The products are afterward separated by distillation, and the catalyst recycled.

The catalyst can be reacted either without solvent or in the presence of a fluid solvent or diluent medium. Suitable solvents can be used from among ethers, nitrites, halogenated solvents, aliphatic or aromatic hydrocarbons, esters, secondary and tertiary alcohols, and ketones, polar aprotic solvents, and among combinations of two or more of these. Reacting without solvent (i.e., in the MeOH/PO mix) is preferred. The chosen MeOH:PO ratio is in the range 0.5 mol/mol–5 mol/mol (preferred range: 0.8–2 mol/mol, especially 0.9–1.5 mol/mol).

Reaction takes place generally at moderate temperatures, i.e., in the range –20–120° C., more preferably 0–60°C.

Further details on solvents good to use in the context of the present invention and on the reaction temperature can be found in WO 00/09463, especially pp. 55/56 therein.

For the purposes of the present invention, the reaction can be carried out continuously or batchwise. It can be carried out in one or more reactors or reaction zones. The catalyst can either be used as such in homogeneous form or as a suspension. It can also be used in immobilized form on a matrix.

The propylene oxide used as starting material in the process of the present invention is likewise subject to no particular restrictions. Particular preference is given to using a propylene oxide which has been obtained using a zeolite catalyst, in particular a zeolite catalyst of the TS-1 type. The preparation of propylene oxide using such a catalyst is described, inter alia, in EP-A 0 100 119 and also patent applications of the present applicant, e.g. DE-A 10001401.1, DE-A 198 35 907, DE-A 199 36 547, DE-A 100 15 246.5, DE-A 10032884.9, DE-A 10105527.7, DE-A 19847629.9 and DE-A 100 32 885.7 and the prior art cited therein, whose relevant contents are hereby fully incorporated into the disclosure of the present patent application.

Furthermore, the present invention provides novel racemic mixtures of catalytically active compounds which can readily be used for the purposes of the present invention and have, in particular, tetradentate ligands which are substituted by monoisobutylene, oligoisobutylene or polyisobutylene groups in certain positions defined in more detail below.

The present inventoin thererfore also provides racemic mixtures of at least one compound having the following formula (A'):

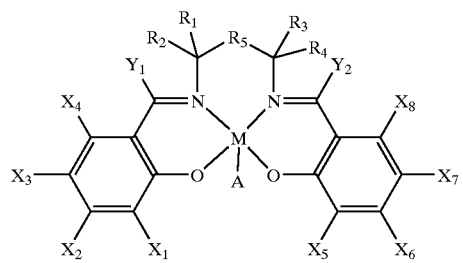

where the substituents $R_1$, $R_2$, $R_3$, $R_4$, $R_5$, $Y_1$, $Y_2$, A and M are as defined in claim 5, $X_2$, $X_4$, $X_6$ and $X_8$ are each hydrogen and $X_1$, $X_3$, $X_5$ and $X_7$ are each, independently of one another, a monoisobutylene, oligoisobutylene or polyisobutylene group.

A racemic mixture as defined above in which the carbocycles or heterocycles within the compounds are substituted by an oligoisobutylene or polyisobutylene group having from 2 to 1000 repeating units.

A racemic mixture comprising at least one of the following compounds (A'1) to (A'4):

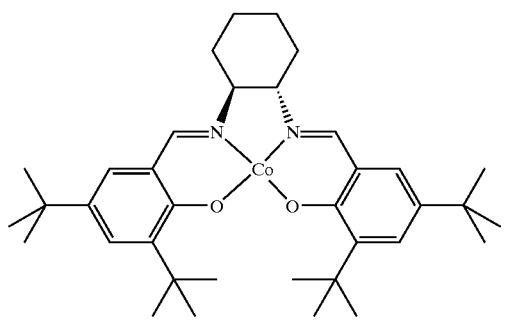

A'1

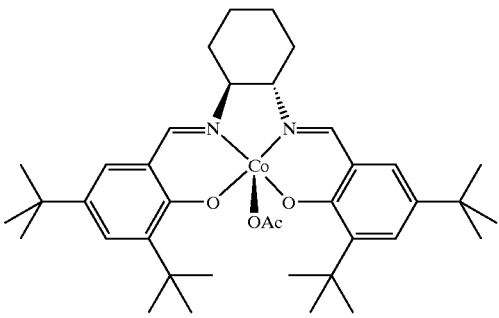

A'2

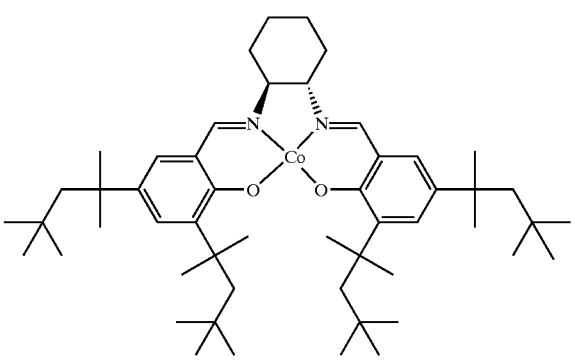

A'3

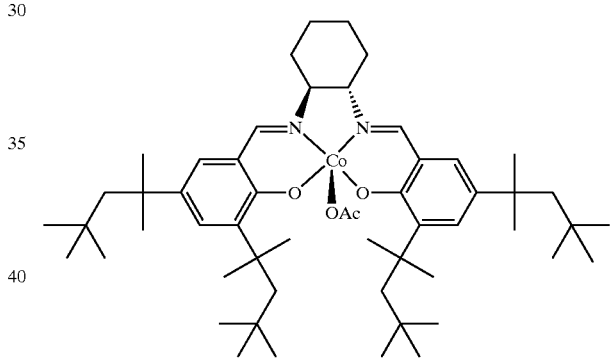

A'4

EXAMPLES

Example 1

Preparation of rac-1,2-bis(3,5-di-tert-butylsalicylamino) cyclohexane (Salen 1)

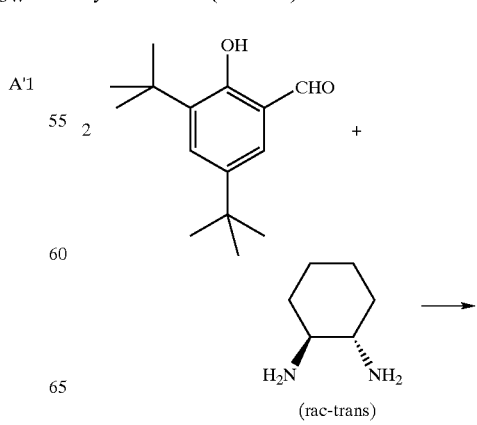

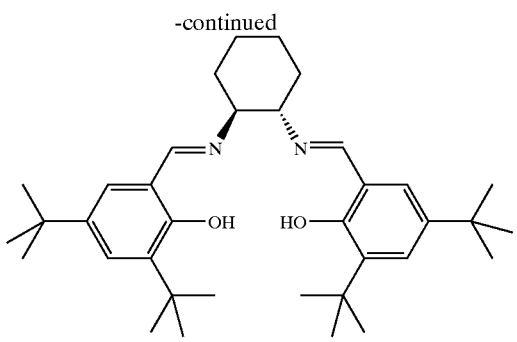

Rac-trans-1,2-diaminocyclohexane (6.09 g, 53 mmol) was dissolved in 300 ml of ethanol and placed in a three-necked flask fitted with a mechanical stirrer. 3,5-Di-tert-butylsalicylaldehyde (25.0 g, 107 mmol) was then added. The mixture was subsequently refluxed for one hour, forming a red suspention. After cooling, about 100 ml of water were added dropwise while stirring. The precipitate formed was filtered off and washed with a small portion of 95% strength ethanol, giving 29.8 g of crude product. This was purified by recrystallizing it once from 350 ml of ethanol. This gave 27.18 g of pure product as a yellow powder. The yield was 94%.

The product has a melting point of 183° C. and displayed a correct elemental analysis and $^{13}C$— and $^{1}$—H—NMR data.

Example 2
Preparation of the Co(II) Complex of Salen 1

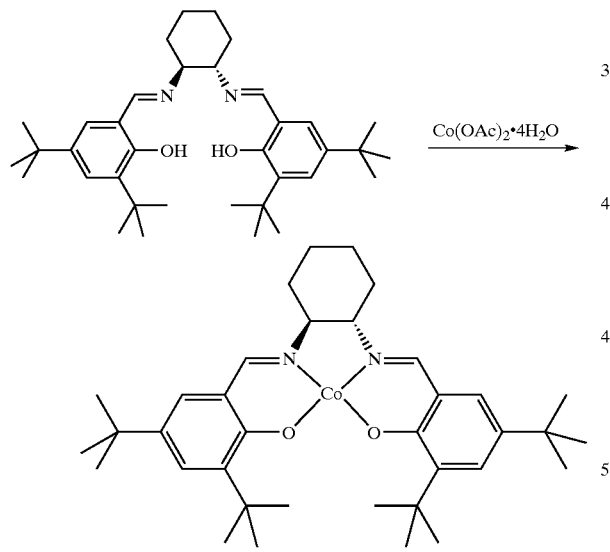

The salen 1 from Example 1 (27.13 g, 50 mmol) was dissolved in toluene (140 g) and freed of dissolved oxygen by means of a gentle stream of $N_2$. A likewise $O_2$-free solution of cobalt(II) acetate tetrahydrate (14.84 g, 59.6 mmol) in methanol (530 ml) was then added and the mixture was stirred under $N_2$ for one hour at room temperature. The precipitate formed was filtered off and washed with a small portion of methanol. This gave 23.46 g of the cobalt(II)-salen complex as a red solid (this solid can be stored without problems in a tightly closed bottle without particular measures to provide inert conditions). The yield was 78%.

The product displayed a correct elemental analysis. Melting point: 183° C.

Example 3

Preparation of the Co(III)-acetato Complex of Salen 1

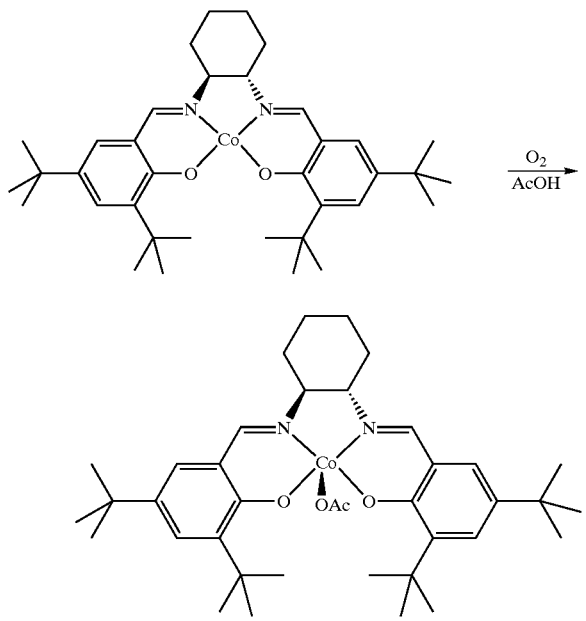

The cobalt(II) complex of salen 1 from Example 2 (1.2 g, 2.2 mmol) was dissolved in toluene (15 ml). Acetic acid (0.12 ml) was added and the mixture was stirred in air for about 10 minutes, resulting in the color of the solution changing from red to brown. The solution was then evaporated on a rotary evaporator and the residue was dried overnight under reduced pressure at room temperature. The crude product (1.62 g, still contains a small amount of toluene) can be used as catalyst without further purification.

Example 4a

Addition of methanol onto propylene oxide using the Co(III)-acetato complex of salen 1 as catalyst (without solvent)

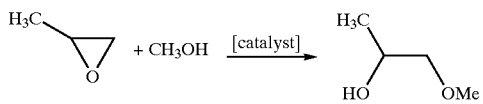

The crude product from Example 3 was suspended in a mixture of propylene oxide (29.0 g, 0.5 mol) and methanol (16.0 g, 0.5 mol) and this suspension was stirred for 10 days at room temperature. The product solution contained, apart from unreacted propylene oxide and methanol, only 1-methoxy-2-propanol (about 8% by weight) and traces of 2-methoxy-1-propanol. The selectivity to 1-methoxy-2-propanol was 98.2%.

Example 4b

Addition of methanol onto propylene oxide using the Co(III)acetato complex of salen 1 as catalyst (with solvent)

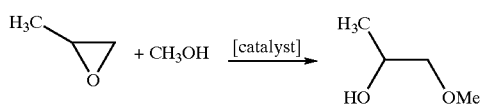

The crude product from Example 3 was suspended in a mixture of propylene oxide (29.0 g, 0.5 mol), methanol (16.0 g, 0.5 mol) and acetonitrile (20 ml) and this suspension was stirred for 14 days at room temperature. The product solution contained, apart from unreacted propylene oxide and methanol, only 1-methoxy-2-propanol (about 12.5% by weight) and traces of 2-methoxy-1-propanol. The selectivity to 1-methoxy-2-propanol was 98.1%.

Example 5

Preparation of 3,5-bis(1,1,3,3-tetramethylbutyl) salicylaldehyde

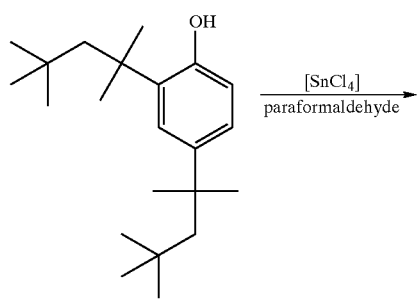

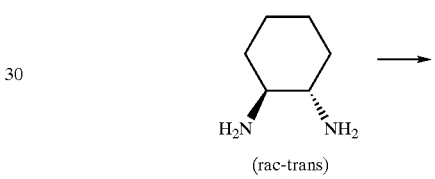

2,4-bis(1,1,3,3-tetramethylbutyl)phenol (26.2 g, 82.4 mmol, synthesized by the method described in U.S. Pat. No. 3,373,210), toluene (200 ml) and 2,6-lutidine (14.4 g, 135 mmol) was placed in a stirred flask under a blanket of nitrogen and the mixture was cooled to 0° C. SnCl$_4$ (8.57 g, 33 mmol) was then carefully added. The mixture was subsequently stirred at room temperature for 20 minutes, before paraformaldehyde (15.1 g, 502 mmol) was added. The mixture was then stirred at 100° C. for 12 hours. After cooling, hydrochloric acid (1 M, 272 ml) was added. The resulting suspension was filtered through Celite and the solid was washed with 100 ml of ethyl acetate. The organic phase of the filtrate was then separated off, washed twice with 100 ml of NaCl solution, dried over MgSO$_4$ and evaporated at reduced pressure. A slightly yellowish oil was formed as product. According to GC/MS, this crude product contains only about 3% of starting material. Yield: 26.9 g (94%).

Example 6

Preparation of rac-1,2-bis(3,5-dioctylsalicylamino) cyclohexane (Salen 2)

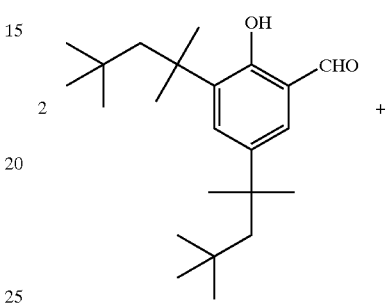

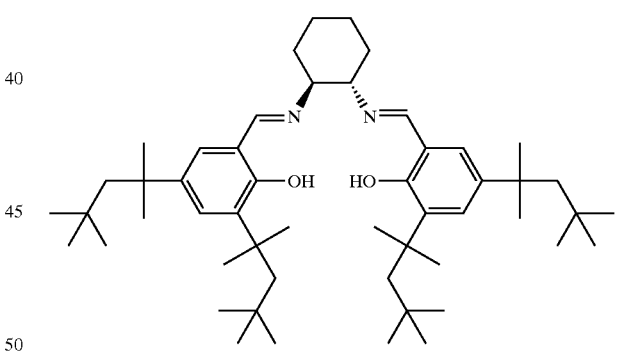

rac-trans-1,2-Diaminocyclohexane (4.16 g, 36.5 mmol) was dissolved in 180 ml of ethanol and placed in a three-necked flask fitted with a mechanical stirrer. 3,5-Dioctylsalicylaldehyde (25.7 g, 74.4 mmol, from Example 5) was then added. The mixture was then refluxed for one hour, forming a yellow suspension. After cooling, about 100 ml of water were added dropwise while stirring. The precipitate formed was filtered off, washed with a small portion of an ethanol/water mixture (1:1) and dried at 70° C. under reduced pressure. This gave a yellow crystalline powder as product. The yield was 24.5 g (93%). The product had a melting point of 172° C. and displayed a correct elemental analysis and $^{13}$C— and $^1$H-NMR data.

Example 7
Preparation of the Co(II) Complex of Salen 2

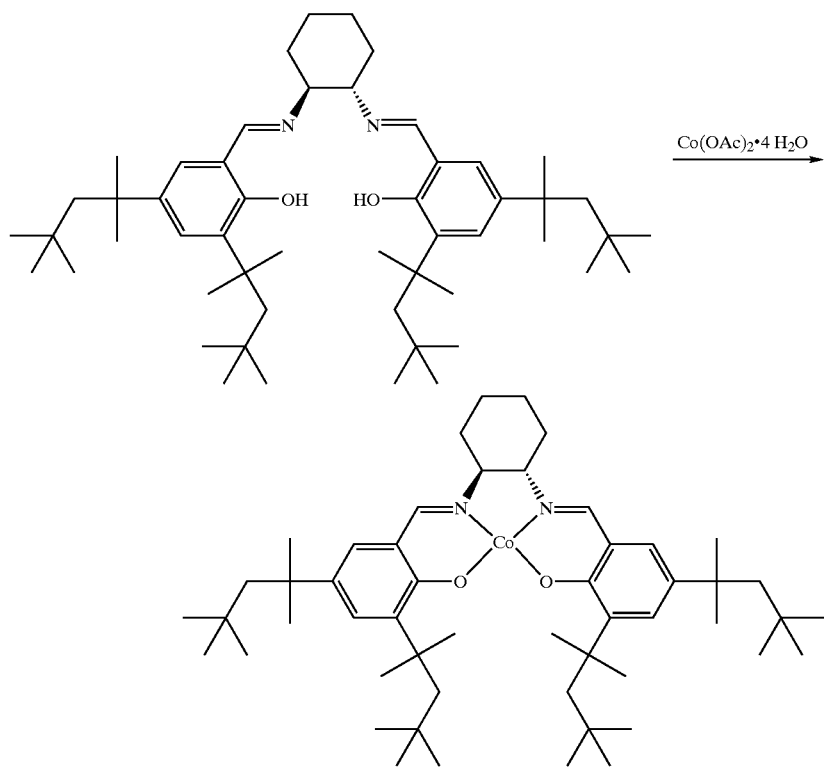

The salen 2 from Example 6 (19.4 g, 27 mmol) was dissolved in toluene (100 g) and freed of dissolved oxygen by means of a gentle stream of $N_2$. A likewise $O_2$-free solution of cobalt(II) acetate tetrahydrate (8.01 g, 32 mmol) in methanol (380 ml) was then added and the mixture was stirred under $N_2$ for one hour at room temperature. The precipitate formed was filtered off and washed with a small portion of methanol. This gave 16.36 g of the cobalt(II)-salen complex as a red solid (this solid can be stored without problems in a tightly closed bottle without any particular measures to produce inert conditions). Yield: 78%.

The product displayed a correct elemental analysis. APCI-MS: 828.7; calc. for [M+H]: 828.6

Example 8
Preparation of the Co(III)-acetato Complex of Salen 2

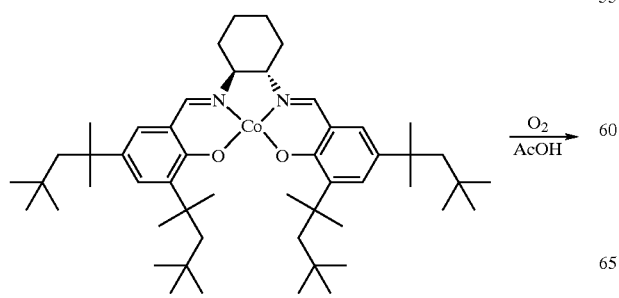

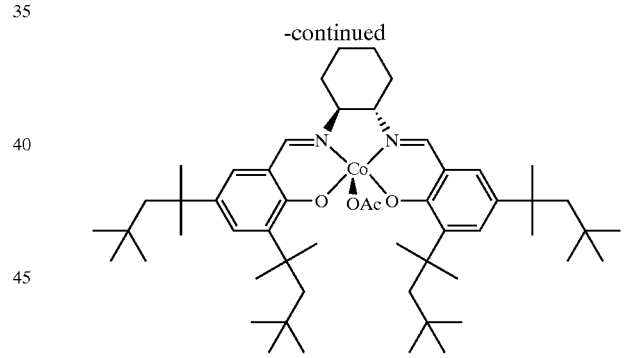

The cobalt(II) complex of salen 2 from Example 7 (1.7 g, 2.2 mmol) was dissolved in toluene (15 ml). Acetic acid (0.12 ml) was added and the mixture was stirred in air for about 10 minutes, resulting in a change in the color of the solution from red to brown. The solution was then evaporated on a rotary evaporator and the residue was dried overnight at room temperature under reduced pressure. The crude product (1.9 g, still contained small amounts of toluene) can be used as catalyst without further purification.

Example 9

Addition of methanol onto propylene oxide using the Co(III)-acetato complex of salen 2 as catalyst

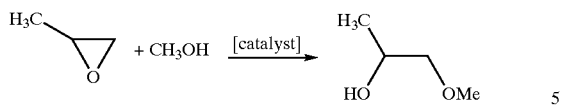

The crude product from Example 8 was suspended in a mixture of propylene oxide (29.0 g, 0.5 mol) and methanol (16.0 g, 0.5 mol) and this suspension was stirred for 10 days at room temperature. The product solution contained, apart from unreacted propylene oxide and methanol, only 1-methoxy-2-propanol (0.5% by weight) and traces of 2-methoxy-1-propanol. The selectivity to 1-methoxy-2-propanol was >95%.

I claim:

1. A selective process for preparing 1-methoxy-2-propanol comprising:

reacting propylene oxide with methanol in the presence of a racemic catalyst which comprises an asymmetric polydentate (tetradentate) ligand complexed with a metal atom, where the complex has an approximately planar geometry, wherein the catalyst has the following formula (B):

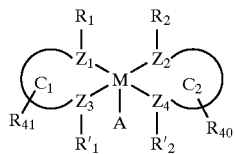

where
- $Z_1$, $Z_2$, $Z_3$ and $Z_4$ are each, independently of one another, a Lewis base;
- the $C_1$ moiety, viewed as a combination of $Z_1$, $Z_3$ and M, and the $C_2$ moiety, viewed as a combination of $Z_2$, $Z_4$ and M, in each case form, independently of one another, a heterocycle;
- $R_1$, $R_2$, $R'_1$ and $R'_2$ in each case independently of one another, are either absent or represent a covalently bound organic or inorganic substituent, in each case depending on the valence of the electron-donating atom to which they are bound;
- $R_{40}$ and $R_{41}$, in each case independently of one another, are either absent or represent one or more covalently bound organic or inorganic substituents on $C_1$ and $C_2$, depending on the valence of the ring atom to which they are bound, or two or more of $R_1$, $R_2$, $R'_1$, $R'_2$, $R_{40}$ and $R_{41}$ together form a bridging substituent;
- with the proviso that $C_1$ is substituted in at least one position by $R_1$, $R'_1$ or $R_{41}$ and $C_2$ is substituted in at least one position by $R_2$, $R'_2$ or $R_{40}$, and at least one of $R_1$, $R'_1$ and $R_{41}$ together with at least one of $R_2$, $R'_2$ and $R_{40}$ form a bridging substituent, where $Z_1$, $Z_2$, $Z_3$ and $Z_4$ are present as a tetradentate ligand;
- M is a metal atom,
- A is a counterion or a nucleophile, and
- the catalyst is present as a racemic mixture.

2. The process of claim 1, wherein the catalyst has the following formula (A):

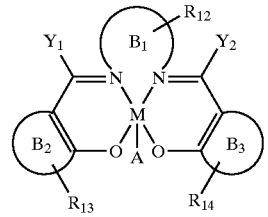

where
- the substituents $R_1$, $R_2$, $Y_1$, $Y_2$, $X_1$, $X_2$, $X_3$ and $X_4$, are each, independently of one another, one of the following groups of atoms: hydrogen, halogen, alkyl, alkenyl, alkynyl, hydroxyl, amino, nitro, diol, amine, imine, amide, phosphoryl, phosphonate, phosphine, carbonyl, carboxyl, silyl, ether, thioether, sulfonyl, selenoether, ketone, aldehyde, ester or $-(CH_2)_m-R_7$,
- where one or more of the abovementioned substituents may together form a carbocyclic or heterocyclic ring having from $_4$ to $_8$ atoms in the ring,
- with the proviso that to form β-iminocarbonyls as tetradentate ligands to which they are bound, at least one of $R_1$, $Y_1$, $X_1$ and $X_2$ is covalently bound to at least one of $R_2$, $Y_2$, $X_3$ and $X_4$, and
- at least one of $Y_1$ and $Y_2$ is hydrogen;
- $R_7$ is an aryl, cycloalkyl or cycloalkenyl group, a heterocyclic group or a polycyclic group;
- m is an integer in the range from 0 to 8;
- M is a metal atom;
- A is a counterion or a nucleophile; and
- the catalyst is present as a racemic mixture.

3. The process of claim 1, wherein the catalyst has the following formula (C):

where
- the B moiety is a bridging substituent of the diimine type, represented by $-R_{15}-R_{16}-R_{17}$, where $R_{15}$ and $R_{17}$, in each case independently of one another, are absent or represent an alkyl, alkenyl or alkynyl group and $R_{16}$ is either absent or is an amine, imine, amide, phosphoryl, carbonyl, silyl, oxygen, sulfur, sulfonyl, selenium or ester group or atom;
- $B_2$ and $B_3$ are each, independently of one another, rings selected from the group consisting of cycloalkyl, cycloalkenyl, aryl and heterocyclic rings, where the rings have from 4 to 8 atoms in the ring;
- $Y_1$ and $Y_2$ are each, independently of one another, hydrogen, halogen, alkyl, alkenyl, alkynyl, hydroxyl, amino, nitro, diol, amine, imine, amide, phosphoryl, phosphonate, phosphine, carbonyl, carboxyl, silyl, ether, thioether, sulfonyl, selenoether, ketone, aldehyde, ester or $-(CH_2)_m-R_7$ groups or atoms;
- $R_{12}$, $R_{13}$ and $R_{14}$, in each case independently of one another, are absent or represent one or more covalently bound halogen, alkyl, alkenyl, alkynyl, hydroxyl, amino, nitro, diol, amine, imine, amide, phosphoryl, phosphonate, phosphine, carbonyl, carboxyl, silyl, ether, thioether, sulfonyl, selenoether, ketone, aldehyde, ester or —(CH$_2$)$_m$—R$_7$ substituents on B$_1$, B$_2$ and B$_3$, where R$_{12}$ may occur at one or more positions on R$_{15}$—R$_{16}$—R$_1$—, or two or more of the groups R$_{12}$, R$_{13}$, R$_{14}$, Y$_1$ and Y$_2$ together form a bridging substituent;

R$_7$ is an aryl, cycloalkyl or cycloalkenyl group, a heterocyclic group or a polycyclic group;

m is an integer in the range from 0 to 8;

M is a metal atom;

A is a counterion or a nucleophile; and the catalyst is present as a racemic mixture.

4. The process of claim 1, wherein the catalyst has the following formula (D):

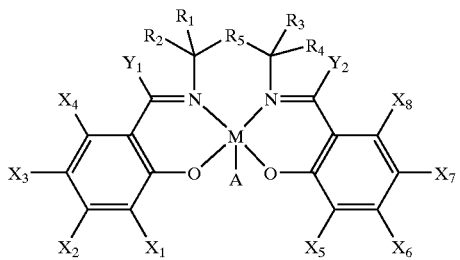

where the substituents R$_1$, R$_2$, R$_3$, R$_4$, R$_5$, Y$_1$, Y$_2$, X$_1$, X$_2$, X$_3$, X$_4$, X$_5$, X$_6$, X$_7$ and X$_8$ are each, independently of one another, hydrogen, halogen, alkyl, alkenyl, alkynyl, hydroxyl, amino, nitro, diol, amine, imine, amide, phosphoryl, phosphonate, phosphine, carbonyl, carboxyl, silyl, ether, thioether, sulfonyl, selenoether, ketone, aldehyde, ester or —(CH$_2$)$_m$—R$_7$ groups or atoms;

or two or more of the substituents together form a carbocycle or heterocycle having from 4 to 10 atoms in the ring;

R$_7$ is an aryl, cycloalkyl or cycloalkenyl group, a heterocyclic group or a polycyclic group;

m is an integer in the range from 0 to 8;

M is a metal atom;

A is a counterion or a nucleophile;

where, if R$_5$ is absent, at least one of R$_1$ and R$_2$ together with at least one of R$_3$ and R$_4$ form a bridging substituent; and the catalyst is present as a racemic mixture.

5. The process of claim 1, wherein the catalyst is in the form of a monomer or an oligomer having from 2 to 20 repeating units.

6. The process of claim 1 which is carried out in a liquid medium which is different from propylene oxide and methanol.

7. The process of claim 1 which is carried out at a temperature from 0 to 120° C.

8. The process of claim 1, wherein the catalyst has been immobilized on a matrix.

9. The process of claim 1, wherein said reaction occurs in the absence of solvent (in the MeOH/PO mixture).

10. The process of claim 9, wherein the MeOH:PO ratio ranges from 0.5 mol/mol–5 mol/mol.

11. The process of claim 9, wherein the MeOH:PO ratio ranges from 0.8–2 mol/mol.

12. The process of claim 9, wherein the MeOH:PO ratio ranges from 0.9–1.5 mol/mol.

13. The process of claim 1, wherein said reaction occurs in the presence of at least one solvent selected from the group consisting of ether(s), nitrile(s), halogenated solvent(s), aliphatic or aromatic hydrocarbon(s), ester(s), secondary alcohol(s), tertiary alcohol(s), ketone(s), and polar aprotic solvent(s).

14. The process of claim 1, wherein the selectivity of reaction to 1-methoxy-2-propanol is greater than 95%.

15. The process of claim 1, wherein the selectivity of reaction to 1-methoxy-2-propanol is greater than 98.1%.

16. The process of claim 1 further comprising separating the 1-methoxy-2-propanol by distillation and optionally recycling the catalyst.

17. The process of claim 1, further comprising using the 1-methoxy-2-propanol as a starting material for a preparative process.

18. The process of claim 1, wherein M is Cr, Mn, V, Fe, Co, Mo, W, Ru or Ni.

19. The process of claim 1, wherein M is Cr(III) or Co(III).

20. The process of claim 1, wherein A is a nucleophile containing oxygen.

21. The process of claim 1, wherein A is a carboxylate.

22. The process of claim 1, wherein Z$_1$ and Z$_2$ are N, Z$_3$ and Z$_4$ are O, and C$_1$ and C$_2$ are six-membered rings.

23. The process of claim 1, wherein Z$_1$ and Z$_2$ are N, Z$_3$ and Z$_4$ are O, C$_1$ and C$_2$ are six-membered rings, wherein two R$_{40}$ together form a bridging substituent, and wherein two R$_{41}$ together form a bridging substituent.

24. The process of claim 1, wherein Z$_1$ and Z$_2$ are N, Z$_3$ and Z$_4$ are O, C$_1$ and C$_2$ are six-membered rings and R$_1$ and R$_2$ together form a bridging substituent.

* * * * *